(12) United States Patent
Alberti et al.

(10) Patent No.: US 8,703,059 B2
(45) Date of Patent: Apr. 22, 2014

(54) COMBUSTION ANALYSIS APPARATUS AND METHOD

(75) Inventors: David Marco Gertruda Alberti, Pijnacker (NL); Maurice Stephan Van Doeselaar, Haarlem (NL)

(73) Assignee: Thermo Fisher Scientific Inc., Waltham, MA (US)

( * ) Notice: Subject to any disclaimer, the term of this patent is extended or adjusted under 35 U.S.C. 154(b) by 951 days.

(21) Appl. No.: 11/967,609

(22) Filed: Dec. 31, 2007

(65) Prior Publication Data

US 2008/0213913 A1 Sep. 4, 2008

(30) Foreign Application Priority Data

Dec. 29, 2006 (GB) .................................. 0626032.7

(51) Int. Cl.
*G01N 31/12* (2006.01)

(52) U.S. Cl.
USPC ......... 422/78; 422/80; 422/82.07; 422/82.08; 422/83; 422/186.07; 422/186.3; 436/122; 436/123; 436/174

(58) Field of Classification Search
None
See application file for complete search history.

(56) References Cited

U.S. PATENT DOCUMENTS

| | | | |
|---|---|---|---|
| 4,297,123 A | 10/1981 | Wyse et al. | |
| 4,879,246 A | 11/1989 | Puschel et al. | |
| 5,047,127 A | 9/1991 | Tottori et al. | |
| 5,424,217 A * | 6/1995 | Benner et al. | 436/123 |
| 5,531,105 A * | 7/1996 | Leong et al. | 73/114.56 |
| 5,771,693 A * | 6/1998 | Coney | 60/407 |
| 5,853,684 A * | 12/1998 | Fang et al. | 423/244.1 |
| 6,458,328 B1 | 10/2002 | Wreyford | |
| 6,875,008 B1 | 4/2005 | Martin et al. | |
| 2003/0049855 A1* | 3/2003 | Rhodes | 436/117 |
| 2003/0133836 A1 | 7/2003 | Mueller et al. | |
| 2004/0015630 A1 | 1/2004 | Boolos et al. | |
| 2004/0151630 A1 | 8/2004 | Hernandez, Jr. et al. | |
| 2005/0074365 A1 | 4/2005 | Olstowski | |

FOREIGN PATENT DOCUMENTS

| | | |
|---|---|---|
| DE | 4039791 | 6/1992 |
| DE | 4231510 A1 | 11/1993 |
| DE | 29918373 | 10/1999 |
| EP | 1630133 | 3/2006 |
| GB | 116503 | 9/1920 |

(Continued)

OTHER PUBLICATIONS

Great Britain Search Report for 0626032.7 dated Aug. 10, 2007.

(Continued)

*Primary Examiner* — Robert Xu
(74) *Attorney, Agent, or Firm* — Thomas F. Cooney; Charles B. Katz; Haynes and Boone, LLP

(57) ABSTRACT

A method and apparatus for combustion analysing a sample in a combustion analyzer (120,160,180), where the sample comprises a proportion of sulphur. The sample is supplied to the combustion analyzer and combusted to produce combustion products, comprising a yield of sulphur dioxide for detection. Nitrogen monoxide or a source of nitrogen monoxide is supplied to the combustion analyzer to improve the yield of sulphur dioxide in the combustion products. The yield improver may be supplied before and/or during the combusting step. A proportion of yield improver is preferably greater than the (expected) proportion of sulphur. Ozone may be supplied to the combustion products to convert at least a proportion of any nitrogen monoxide in the combustion products to nitrogen dioxide, before detection.

10 Claims, 8 Drawing Sheets

(56) References Cited

FOREIGN PATENT DOCUMENTS

| | | |
|---|---|---|
| GB | 269046 | 4/1927 |
| GB | 2037425 | 7/1980 |
| JP | 58122458 | 1/1982 |
| JP | 57037258 | 3/1982 |
| JP | 59083054 | 5/1984 |
| JP | 04151535 | 10/1990 |
| JP | 2000-155117 A | 6/2000 |
| JP | 2000155117 | 6/2000 |
| SU | 1762200 | 9/1992 |
| WO | 90/06508 | 6/1990 |

OTHER PUBLICATIONS

European Search Report for 0626032.7 dated Aug. 15, 2007.
Glarborg et al., "Impact of SO2 and NO on CO Oxidation Under Post-Flame Conditions," International Journal of Chemical Kinetics, Oct. 1996, vol. 28, No. 10, pp. 773-790.
Van Der Saar, "Sulfur Analysis—for Now and in the Future", Thermo Electron Corporation, Oct. 2005.
Smith, "Principles of Ozone Generation", Wartec Engineering Pty Ltd, 2007.
Great Britain Search Report for 0626031.9 dated Aug. 10, 2007.
European Search Report for 0626031.9 dated Aug. 21, 2007.
David Marco Gertruda Alberti and Louis Marie Smeets, U.S. Appl. No. 11/967,625 filed Dec. 31, 2007 for "Apparatus and Method for Generating Nitrogen Oxides".
European Search Report issued by the European Patent Office on Mar. 18, 2008 for European Patent Application No. 08250006.7, (4 pages).
European Search Report issued by the European Patent Office on Mar. 5, 2008 for European Patent Application No. 08250005.9, (3 pages).
"U.S. Appl. No. 11/967,625: Office Action mailed Jun. 18, 2009 Jan. 6, 2010," 11 pages.
"U.S. Appl. No. 11/967,625: Office Action mailed Jan. 6, 2010," 10 pages.

* cited by examiner

COMBUSTION ANALYSIS APPARATUS AND METHOD

CROSS REFERENCE

This application claims priority benefit of Great Britain Patent Application Number 0626032.7, filed Dec. 29, 2006.

Reference is made to a co-pending application, entitled "Apparatus and method for generating nitrogen oxides", filed on Dec. 31, 2007, under U.S. application Ser. No. 11/967,625 and claiming priority from GB0626031.9, the entirety of which is incorporated herein by this reference.

FIELD OF THE INVENTION

The invention relates to an apparatus and method for the combustion analysis of samples; in particular, total sulphur analysis of samples comprising a proportion of sulphur.

BACKGROUND OF THE INVENTION

Combustion analyzers are used to determine the concentration of one or more components of a sample, by combusting the sample and analysing the gaseous products for specific oxides. Typically, the carbon, sulphur and/or nitrogen content of the sample is measured by detecting $CO_2$, $SO_2$ and NO, respectively.

A schematic illustration of a typical combustion analyzer is shown in FIG. 1. The combustion analyzer 10 comprises a sample introduction stage 20, a combustion stage 30, a conditioning stage 40, and a detection stage 50. The sample introduction stage 20 comprises a sample introduction apparatus 22, to which are connected a supply of a sample 24, a supply of oxygen 26 and a supply of argon 27. The sample introduction apparatus 22 introduces these fluids into a combustion chamber 32 in a suitable form for combustion to take place. A further supply of oxygen 25 may be provided, directly into the combustion chamber 32. The combustion chamber 32 is heated by an electric heater 34, so that the sample is delivered into an oxygen-rich atmosphere at high temperature, typically of around 1000° C. The sample is thereby converted into various combustion products, such as $CO_2$, $H_2O$, $SO_2$, NO, etc. The combustion products leave the combustion chamber 32 and pass through the conditioning stage 40, where processes such as cooling, filtering, drying, etc. take place. The conditioned products then pass through one or more dedicated detectors 52, 54, in which properties of the components of the combustion products may be detected. For example, $CO_2$ may be detected by absorption of infrared radiation, using a non-dispersive infrared (NDIR) detector; $SO_2$ may be detected by fluorescence with ultraviolet light, using a light sensor; and NO can be detected from de-excitation processes following its reaction with ozone ($O_3$) to form excited $NO_2$, using a chemiluminescence light sensor. The detected signals are indicative of the respective amount of each component of the combustion products and can therefore be related to the composition of the original sample. Finally, the detected combustion products are passed out of the detection stage 50, as waste products 56.

The performance of such a combustion analyzer 10—in terms of its suitability, reliability, accuracy and robustness—depends strongly on its ability to convert the element(s) of interest in a sample into its/their respective oxide(s).

For combustion analysis of a sample containing sulphur, the combustion product to be detected is sulphur dioxide ($SO_2$). The achievable yield of $SO_2$ which may be detected with current combustion analyzers is around 90%. The yield is the proportion of the amount of sulphur originally contained in the sample which is actually converted to sulphur dioxide. The achievable yield of a combustion analyzer is calculated by analysing known, standard samples for calibration purposes. Once a calibration curve has been measured using standard samples, unknown samples may be analyzed and the detected values may be calibrated accordingly. However, samples and also combustion conditions in a combustion analyzer are subject to variation, with the result that the calibration curve cannot consistently provide accurate measurements from sample to sample.

Also, current compliance regulations for sulphur in petrochemical fuels mean that total sulphur specifications (i.e., the permissible amount of sulphur in any form) are at low parts per million (ppm) levels and are heading ever lower, towards sub-ppm levels. For example, diesel specifications for sulphur are soon expected to be 10 ppm in the EU and 15 ppm in the US; for gasoline (petrol), the specifications are expected to be 10 ppm in the EU and 80 ppm in the US. It is therefore increasingly important to be able to measure sulphur concentrations at such low levels.

Accordingly, it would be desirable to provide an improved apparatus and method for combustion analysis of samples containing sulphur.

SUMMARY OF THE INVENTION

According to a first aspect of the invention, there is provided a method of combustion analysing a sample in a combustion analyzer, the sample comprising a proportion of sulphur, the method comprising the steps of: supplying the sample to the combustion analyzer; and combusting the sample to produce combustion products, the combustion products comprising a yield of sulphur dioxide for detection, characterised by the step of supplying a yield improver to the combustion analyzer, wherein the yield improver is nitrogen monoxide or a source of nitrogen monoxide.

According to a second aspect of the invention, there is provided a combustion analyzer for combustion analysing a sample comprising a proportion of sulphur, the analyzer comprising: a combustion chamber for receiving a sample for combustion therein to form combustion products, the combustion products comprising a yield of sulphur dioxide; and a detector for detecting an amount of sulphur dioxide in the combustion products, characterised by further comprising a yield improver supply apparatus for supplying a yield improver to the combustion analyzer, wherein the yield improver is nitrogen monoxide or a source of nitrogen monoxide.

The yield improver is a sulphur dioxide yield improver. By yield improver is meant any substance which, when added to the combustion analyzer, increases the yield of sulphur dioxide in the combustion products to be detected, relative to the yield of sulphur dioxide in the combustion products which would result when the substance is not added to the combustion analyzer. The inventors discovered that adding a particular type of substance to the combustion analyzer increases the yield of sulphur dioxide, after taking steps to remove a substance which the inventors recognised was interfering with the detection of sulphur dioxide in the detector. Tests were carried out on known samples, which were prepared without the interfering substance or a source of the interfering substance, and also on known samples, which were prepared with an amount of the interfering substance, and in both cases steps were taken to remove any interfering substance present, before the combustion products were measured. It was found that the yield of sulphur dioxide was greater in the sample which was combusted with an amount of the interfering substance. The yield improver may be provided by a number of different compounds, some of which result in an interfering substance needing to be removed before detection of the sulphur dioxide, while others do not. Clearly, this not only depends on the yield improver employed, but also on the type of sulphur dioxide detector used following combustion.

By adding a yield improver to the combustion analyzer, the overall yield of sulphur dioxide from a sample can be increased. As such, with samples of low sulphur concentration, a greater quantity of sulphur dioxide, for a given sample volume or mass, will be produced, offering improved detection. Furthermore, depending on the amount of yield improver used for a particular sample, it is possible to provide a consistently greater yield of sulphur dioxide from the sample than previously possible. Thus, the effect of variations between samples and variations in other combustion conditions can be reduced, if not minimised. This can help to ensure that measurements made using the calibration curve are accurate from sample to sample.

The term combustion products is used here to mean any substances present in the combustion analyzer following the combusting step and this may include the sample, the yield improver, and other substances, such as oxygen or a carrier gas, and their respective constituents, both in pre-combustion and post-combustion forms.

Preferably, the yield improver is supplied to the combustion analyzer before and/or during combustion of the sample. This allows the yield improver to have effect while the combustion products are being formed, to help improve the yield from the outset of the combustion process. The mechanism by which the yield improver improves the yield of sulphur dioxide in the combustion gases may be such that the yield improver reduces sulphur trioxide to sulphur dioxide, or inhibits the formation of sulphur trioxide, or promotes the formation of sulphur dioxide, or a combination of these. Accordingly, it is preferred that the yield improver be supplied before or during combustion of a sample, to allow the yield improver to have sufficient opportunity to have effect.

The yield improver may be added in a number of forms and in a number of ways. The yield improver may be a liquid and may be added to the sample either before, or during, its supply to the combustion analyzer. Such spiking of the sample means that the yield improver can be mixed with the sample before combustion has begun, so that the yield improver can act from the early stages of combustion.

Alternatively or additionally, the yield improver may be supplied to the combustion chamber of the combustion analyzer via a dedicated inlet. Thus, a yield improver in gaseous form may be pumped into the combustion chamber, or a yield improver in liquid form may be sprayed into the combustion chamber. Again, such supply may take place before and/or during combustion.

Typically, combustion chambers have one or more inlet ports for receiving a supply of oxygen and a carrier gas, such as argon, respectively. For simple application of the invention to existing combustion analyzers, the yield improver may be connected to the supply line for oxygen or a carrier gas, and carried into the combustion chamber therewith. The connection may be made anywhere along such supply line and is preferably in the form of a two-into-one connector (such as a 'T' piece).

Preferably, the connector or the apparatus connecting the yield improver to a dedicated inlet, or to an oxygen supply line or a carrier gas supply line, is switchable between and on and an off state, so that during analysis of samples for which the yield improver is not required, the supply of the yield improver may be stopped.

The yield improver may be nitrogen monoxide or a source of nitrogen monoxide, which is able to form nitrogen monoxide when supplied to the combustion analyzer, during use. Such a source of nitrogen monoxide may be in gaseous, or liquid, form. Preferably, the source of nitrogen monoxide is one or more of pyridine, benzonitrile, nitrogen dioxide, general nitrogen oxides ($NO_x$), ammonia, 2-ethylhexyl nitrate, and the like.

The inventors recognised that nitrogen monoxide caused an interference with the detection of sulphur dioxide in a UV fluorescence detector, for measuring the sulphur dioxide fluorescent response following UV excitation. Upon removing nitrogen monoxide from the combustion products prior to detecting the response, and conducting a number of tests on a variety of samples to verify the removal of the interfering nitrogen monoxide, the inventors discovered that adding nitrogen monoxide to the combustion analyzer actually improved the yield of sulphur dioxide. When added to the combustion chamber or to the sample, before and/or during combustion, the nitrogen monoxide may act to promote the formation of sulphur dioxide, to inhibit the formation of sulphur trioxide, and/or to reduce any sulphur trioxide formed into sulphur dioxide.

Samples for combustion analysis may be petrochemicals, high-grade chemicals, or food and beverage specimens, for which the concentration of sulphur in the sample may be subject to regulation, so that at least an estimated, or expected, proportion of sulphur may be known before combustion analysis. If the proportion of sulphur is entirely unknown, a first quantity of the sample may be analyzed, to obtain an indication of the proportion of sulphur, so that an expected proportion of sulphur may be known for subsequent analyzes. Preferably, the amount of yield improver supplied to the combustion analyzer is such that a proportion of yield improver in the combustion analyzer is greater than the expected proportion of sulphur in a sample. Advantageously, the proportion of yield improver to the expected proportion of sulphur is greater than 2 to 1. Preferably still, the proportion is greater than 4 to 1. It has been found that, with tests using standard samples, adding a greater proportion of yield improver than the expected (in the case of a standard sample, the known) proportion of sulphur increases the yield of sulphur dioxide. Above a ratio of yield improver to sulphur of about 4 or 5 to 1, it has been found that the yield of sulphur dioxide does not increase so rapidly but starts to level off. By relative proportions, or ratios, of NO to $SO_2$ is meant molar proportions/ratios, and not proportions/ratios based on volume or mass.

It is considered that, for most samples, a proportion of yield improver to the expected proportion of sulphur of up to 1000 to 1 would be sufficient to ensure that an increased and substantially consistent yield of sulphur dioxide is achieved, even taking into account potentially significant variations in the actual proportion of sulphur in different samples. In most cases, a proportion of yield improver to the expected proportion of sulphur of up to 25-50 to 1 would be more than sufficient. Indeed, a ratio of 5 to 1 may be preferable, for example, where large variations in the sulphur content are not expected between samples.

Where the yield improver is nitrogen monoxide, or a source thereof, the combustion products at the detector may comprise nitrogen monoxide. The inventors have found that nitrogen monoxide interferes with the detection of sulphur dioxide, when using a UV fluorescence detector. It is therefore preferable to provide an ozone supply to the combustion products, prior to detection, where nitrogen monoxide would otherwise interfere. Ozone reacts with nitrogen monoxide to form nitrogen dioxide and oxygen, so may be used to remove the NO interference. The ozone is preferably added between the combusting step and the detecting step. The ozone may be added after the combustion chamber or to the detector, or to a location in between, such as the transfer tubing between the chamber and detector.

In this case, an ozone supply apparatus may be fitted to an existing combustion analyzer relatively straightforwardly, by adding a connection into the combustion products line between the combustion chamber and the detector. Preferably, the connector is a two-into-one connector, such as a 'T' piece or the like. Preferably, the ozone is supplied at a rate of between approximately 0.5 to 1 ml/s. Preferably also, the connector or the ozone supply apparatus are switchable between an on and an off state, so that ozone is not supplied when not required.

According to a further aspect of the invention, there is provided a method of combustion analysing a sample in a combustion analyzer, the sample comprising a proportion of sulphur, the method comprising the steps of: supplying the sample to the combustion analyzer; combusting the sample to produce combustion products, the combustion products comprising a yield of sulphur dioxide for detection; and detecting an amount of sulphur dioxide in the combustion products, characterised by the further step of supplying ozone to the combustion products to convert at least a proportion of any nitrogen monoxide present in the combustion products to nitrogen dioxide, the step of supplying ozone taking place between the combusting step and the detecting step.

According to a further aspect of the invention, there is provided a combustion analyzer for combusting a sample comprising a proportion of sulphur, the analyzer comprising: a combustion chamber for receiving a sample for combustion therein to form combustion products, the combustion products comprising a yield of sulphur dioxide; and a detector for detecting an amount of sulphur dioxide in the combustion products, characterised by further comprising an ozone supply apparatus arranged to supply ozone to a region of the combustion analyzer, the region being after the combustion chamber, in the detector or therebetween.

Although efforts are made to flush out a combustion analyzer between samples, it is possible that small amounts of nitrogen-containing substances may remain in the analyzer, or these may be incidentally introduced by the various gas or liquid supplies to the combustion chamber. Accordingly, for cases where the sulphur dioxide detector could be affected by interference from nitrogen monoxide in the combustion products, ozone may be added to the analyzer, before the combustion products are detected, to remove the interfering nitrogen monoxide. In this way, a more accurate measurement of the amount of sulphur dioxide may be made.

Other preferred features and advantages of the invention are set out in the description and in the dependent claims which are appended hereto.

BRIEF DESCRIPTION OF THE DRAWINGS

The invention may be put into practice in a number of ways and some embodiments will now be described, by way of non-limiting example only, with reference to the following figures, in which.

DESCRIPTION OF PREFERRED EMBODIMENTS

Figure 1:
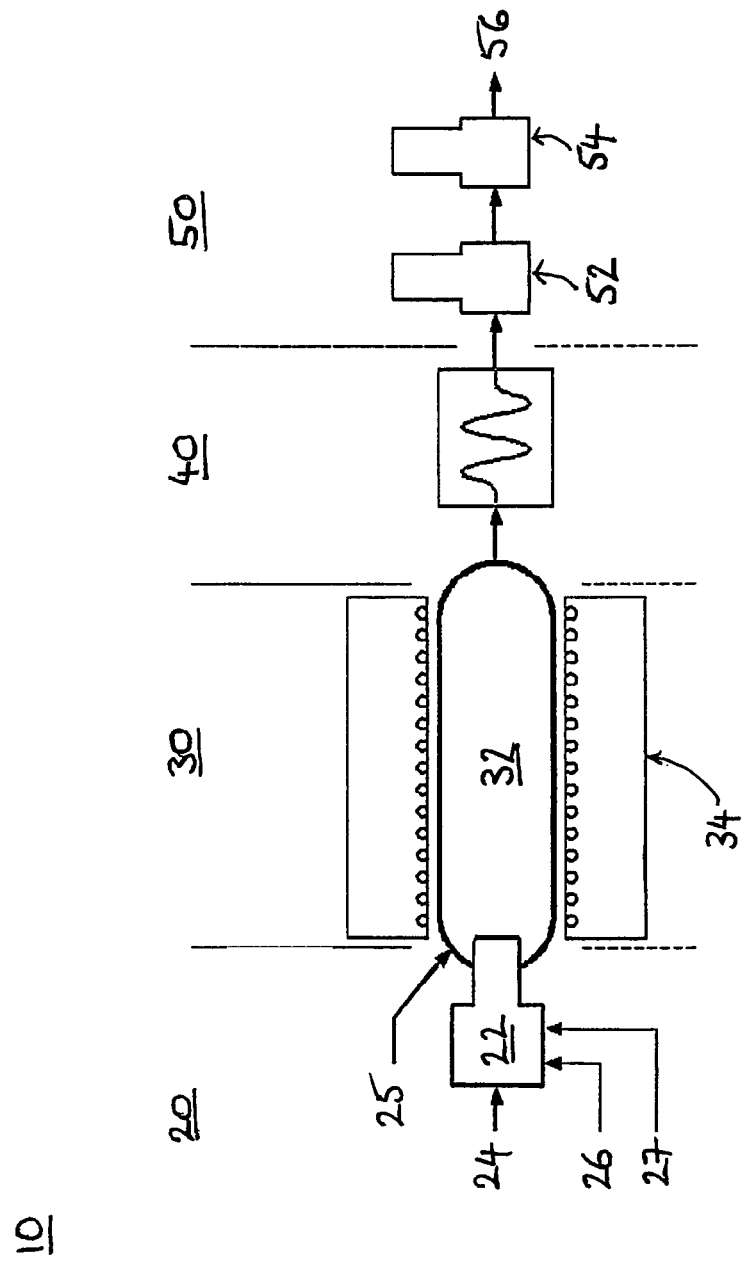
FIG. 1 shows a schematic layout of a typical, prior art combustion analyzer.
Figure 2:
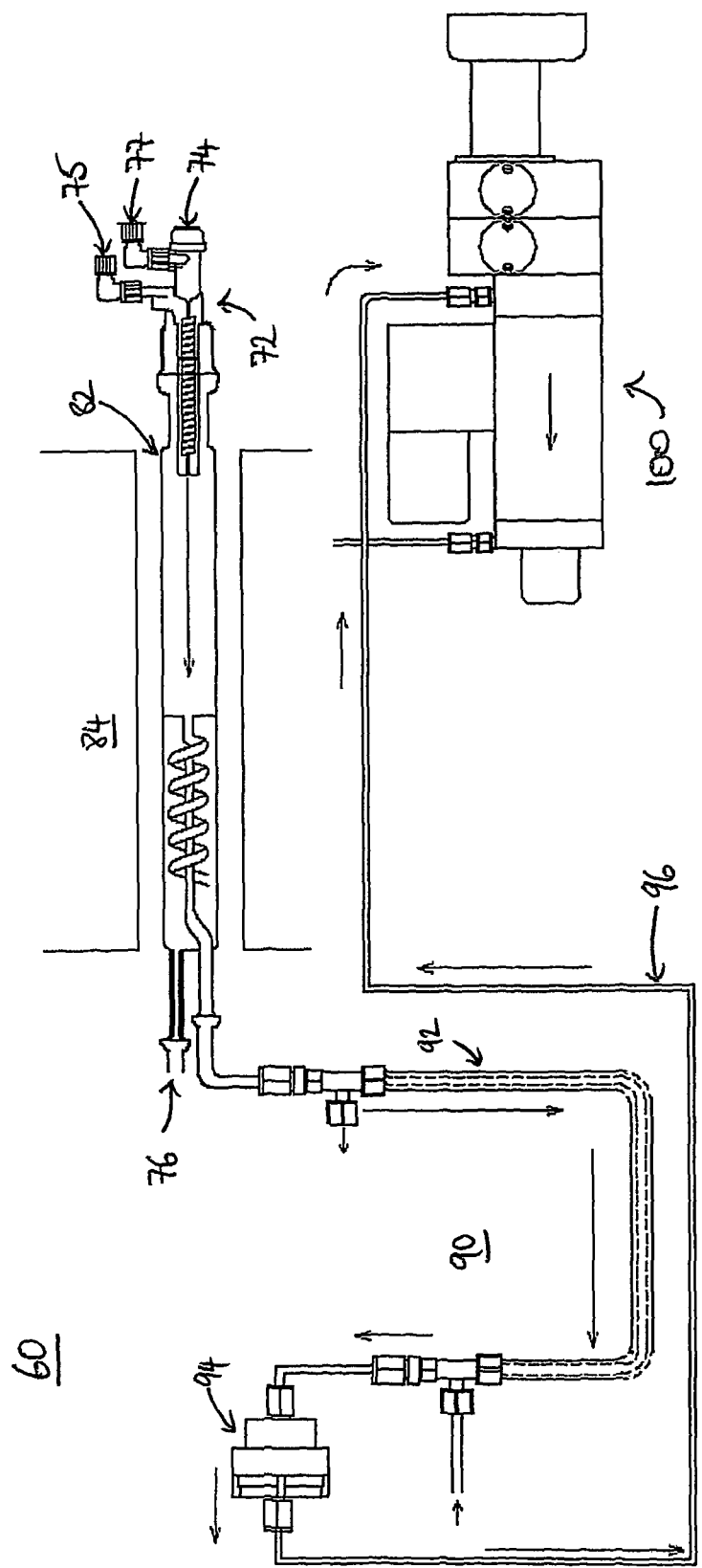
FIG. 2 shows a schematic layout of a prior art, TS3000 combustion analyzer.

Referring to FIG. 2, there is shown schematically the layout of the TS3000 combustion analyzer 60, manufactured by Thermo Fisher Scientific Inc. The combustion analyzer 60 has a sample introduction apparatus 72, which includes a sample supply inlet 74, an oxygen supply inlet 75, and a carrier gas supply inlet 77. The sample introduction apparatus 72 is connected to a combustion chamber 82, which is heated by a heater 84. The combustion chamber 82 is divided into two compartments, the second of which being a turbo compartment and having a further oxygen supply inlet 76, to promote complete combustion of a sample.

Combustion products formed in the combustion chamber 82 pass through a conditioning stage 90, before detection. In this example, the conditioning stage includes a dryer 92, which removes water from the combustion products, the water being entrained by a dry gas flow in the opposite direction to the combustion products, the dry gas flow flowing through an outer tube of the dryer. The conditioning stage also includes a filter 94.

The conditioned combustion products then pass through a combustion product line 96 to a detector. In this example, the detector is a UV fluorescence detector 100.

Total sulphur ultraviolet (TSUV) detection is based on the principle that $SO_2$ molecules fluoresce; i.e., absorb UV light, become excited, then relax to a lower energy state, emitting UV light at a specific wavelength in the process. The emitted light is detected to provide a measure of the amount of $SO_2$ present.

Figure 3:
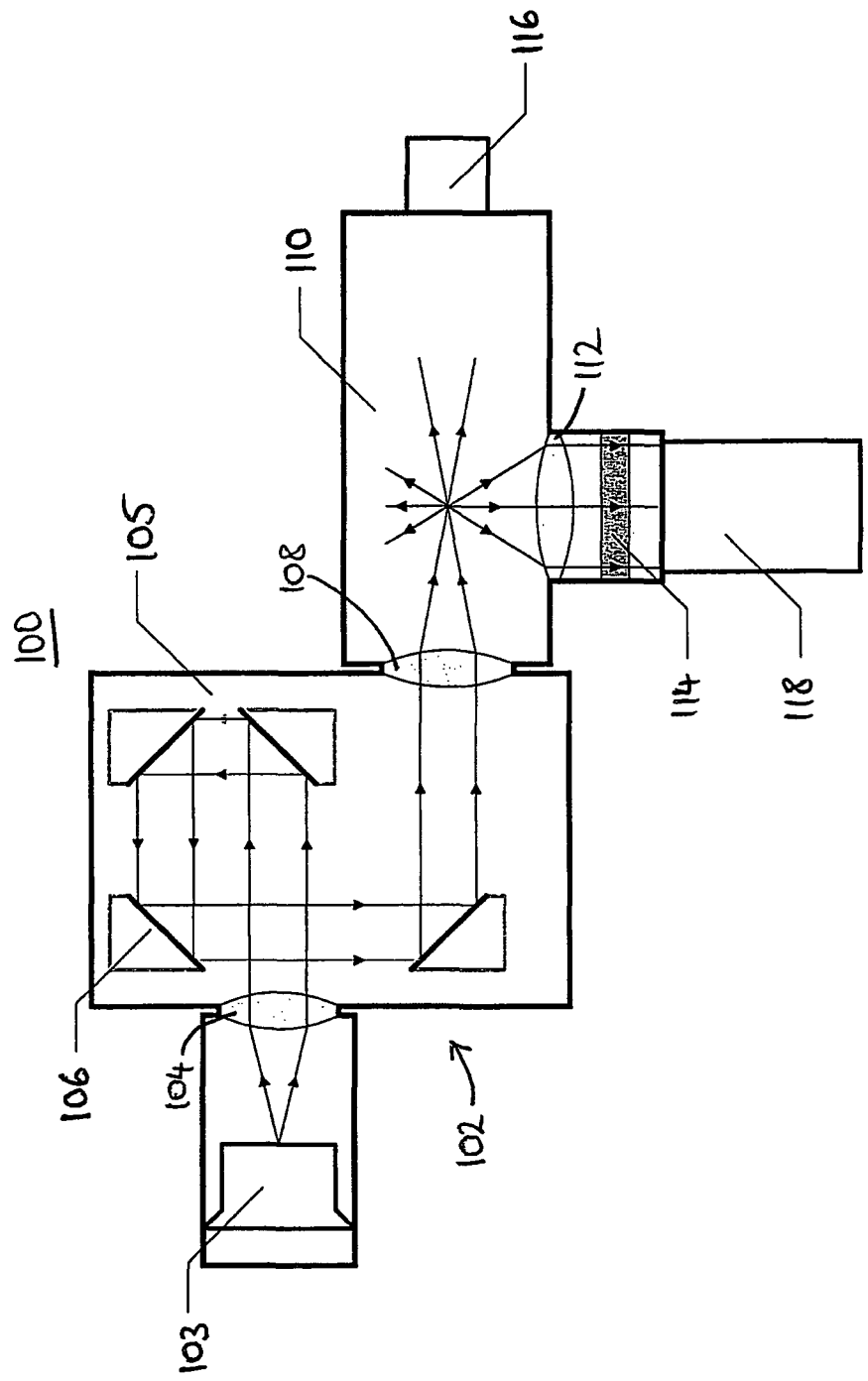
FIG. 3 shows a schematic layout of a prior art UV fluorescence detector.

Referring to FIG. 3, there is shown a schematic layout of a total sulphur ultraviolet (TSUV) detector 100. The detector 100 comprises a light source 102—itself comprising a UV flash lamp 103 and an excitation filter assembly 105—a fluorescence chamber 110 and a UV light sensor 118, preferably a photomultiplier tube (PMT).

The UV flash lamp 103 is arranged to emit one or more light flashes, preferably as a series of pulses. For example, one preferred embodiment has a UV flash lamp which flashes at approximately 10 Hz for the required excitation period. The light produced by the flash lamp 103, which is a broadband source, is directed into the excitation filter assembly 105 by a condenser lens 104. In FIG. 3, the excitation filter assembly 105 comprises four reflecting interference filters 106, although there may be up to eight such filters. The filters 106 receive the light and reflect it around the excitation filter assembly 105 and through a condenser lens 108, into the fluorescence chamber 110. The filters 106 together form a sharp bandpass filter, to ensure that a desired, narrow, UV excitation wavelength range is transmitted into the fluorescence chamber 110.

For the purposes of combustion analysis, $SO_2$ molecules are considered to absorb UV light in the wavelength range of around 190-230 nm. Accordingly, the excitation filter assembly 105 is arranged to pass light with wavelengths falling within, or marginally outside of, this range; for example, wavelengths of 185-235 nm. A narrower range, set about a particular wavelength, may alternatively be selected, if desired.

The condenser lens 108 focuses the pulses of UV light to an excitation region in the fluorescence chamber 110. When the combustion products are transferred by a carrier gas stream into the fluorescence chamber 110, the $SO_2$ present is brought to an excited state by the UV light. The excited state is unstable, so the excited $SO_2$ will very quickly fall back to its ground state, releasing energy in the form of light. The $SO_2$ emission wavelengths are generally longer than the absorption wavelengths and fall in the range of around 220-420 nm.

A proportion of the emitted UV light is directed by a condenser lens 112 onto an emission filter 114. The filter 114 is a band-pass filter, which allows only a wavelength range emitted by excited $SO_2$ molecules to pass through it, towards the UV light sensor 118. The range passed may be the entire $SO_2$ emission range, or may be a selected sub-range in the emission range. The amount of UV light detected by the UV light sensor 118 is proportional to the amount of $SO_2$ in the combustion products. The signal is related to a calibration curve, typically by computer software, to provide a measure of the amount of sulphur present in the sample.

The pulsed UV-fluorescence detector 100 also comprises a reference detector 116, in the fluorescence chamber 110. The reference detector 116 monitors fluctuations in the intensity of the light source 102 (for example, from degradation in the UV flash lamp 103 over time). In this way, either automatic calibration of the measurements may be made during or after detection, or automatic adjustment of the flash lamp voltage may be made during detection.

The inventors have recognised that the readings taken by the above type of detector are not a result purely of $SO_2$ fluorescence. The detector 100 has the disadvantage that it also detects UV light which is emitted from an interfering substance; namely, nitrogen monoxide (NO). It has been found that the detector 100 is unable to distinguish between $SO_2$ and NO, since they both fluoresce upon excitation with UV light in generally the same wavelength range. Accordingly, the inventors have appreciated that measurements made by such a detector may indicate higher levels of $SO_2$ than are actually present in the fluorescence chamber, since NO fluorescence can contribute to the detected signal. Many samples contain a proportion of nitrogen and so can be incorrectly quantified by the detector.

It is understood that NO molecules absorb UV light with absorption peaks generally around 190, 195, 205, 215 and 225 nm. These wavelengths fall within the $SO_2$ absorption range of 190-230 nm. As such, the pulsed UV excitation light may be absorbed by NO, as well as by $SO_2$. It is further understood that NO emits, or fluoresces, at wavelengths in the range of 220-370 nm. These wavelengths fall within the $SO_2$ emission range of 220-420 nm. As such, the emission filter 114 may pass, and the UV light sensor 118 may detect, light emitted by NO, as well as by $SO_2$.

Accordingly, a method for removing the interfering nitrogen monoxide from the combustion products is now discussed, in accordance with one embodiment of the invention.

When it is desired to measure the concentration of nitrogen in a sample, it is known to use a total nitrogen (TN) detector, as mentioned above. This is a chemiluminescence detector, which measures the amount of light emitted when excited nitrogen dioxide falls to its ground state. The excited nitrogen dioxide is formed from the reaction of nitrogen monoxide with ozone ($O_3$). The reaction mechanism used in TN detectors was applied in sulphur dioxide analysis. An ozone feed unit was therefore installed on the combustion products line between the combustion chamber and the detector, so that any nitrogen monoxide in the combustion products would react with the ozone and thereby be removed from the combustion products and not be detected by the sulphur dioxide UV fluorescence detector. The ozone feed unit was configured to supply ozone to the combustion products line at a rate sufficient to remove substantially all of the nitrogen monoxide. For example, for a sample of 100 µl, a flow rate of ozone of 50 ml/min would be sufficient to remove the nitrogen monoxide formed from a nitrogen concentration in the sample of up to 9000 ppm.

Tests were carried out on various standard samples (the concentrations of the various components of which were already known). Some samples were prepared without any nitrogen-containing component (which would form nitrogen monoxide in the combustion chamber), some were prepared with an amount of a nitrogen-containing component, and some were prepared with a nitrogen-containing component only (i.e., no sulphur-containing component). The nitrogen-containing component used was benzonitrile and pyridine in xylene. In each case, an ozone feed unit was used to supply ozone to the combustion products passing through the combustion products line, to remove any nitrogen monoxide before the combustion products reached the detector. Although the concentration of sulphur in the first two types of sample should have been the same, it was detected to be greater in the second type of sample. Accordingly, adding a nitrogen-containing component to the combustion chamber increased the yield of sulphur dioxide. This is evident since, although the nitrogen monoxide interference was removed from the combustion products of all samples, a higher sulphur dioxide reading was obtained from the second type of sample.

Normally, when a sulphur-containing substance is combusted, approximately 90% of the sulphur is formed into sulphur dioxide and approximately 10% is formed into sulphur trioxide ($SO_3$). For this reason, most total sulphur detectors measure sulphur dioxide in one way or another.

Two experiments, using methods and apparatuses according to embodiments of the invention, and their results will now be discussed. The first experiment is discussed with reference to table 1, below, and FIG. 4. In the first experiment, a set of known, standard samples was prepared, as follows. Eight different samples were prepared and each sample contained 10 ppm of a sulphur-containing substance. The samples also contained the following concentration of a nitrogen-containing substance, respectively: 0, 3, 5, 10, 25, 50, 100, and 150 ppm. The nitrogen-containing substance used was pyridine in xylene.

A combustion analyzer to detect $SO_2$ by UV fluorescence detection was modified to allow it to operate under a number of different conditions. The analyzer used was the SphiNCX analyzer, manufactured by Thermo Fisher Scientific Inc. The modifications made were to add a nitrogen oxides ($NO_x$, which may include NO, $NO_2$, $N_2O_3$ etc., in various proportions) feed unit to the oxygen supply line, by means of a switchable connector, and to add an ozone feed unit to the combustion products line, again by means of a switchable connector. The switchable connectors were used so that one or both of the supplies could be turned off, as required.

The following methods of analysis were used with each of the eight samples, respectively. For method A, the analysis was conducted with both the $NO_x$ and $O_3$ supplies turned off;

that is, essentially, the SphiNCX analyzer was operating in its standard manner according to international standard ASTM D5453 for total sulphur determination. For method B, the analysis was conducted with the $O_3$ supply switched on and the $NO_x$ supply switched off. That is, the combustion process was as standard, but substantially all NO in the combustion products was removed. For method C, the analysis was conducted with both $NO_x$ and $O_3$ supplies turned on. That is, the analysis was as standard, but a yield improver gas was supplied to the combustion chamber, along with the oxygen supply, and substantially all NO in the combustion products was removed. When the ozone feed unit was employed, the ozone gas flow rate into the combustion products line was 50 ml/min. When the $NO_x$ feed unit was employed, the $NO_x$ flow rate into the oxygen supply line was between 34 and 40 ml/min. The sulphur-containing liquid used was thiophene.

Figure 4:
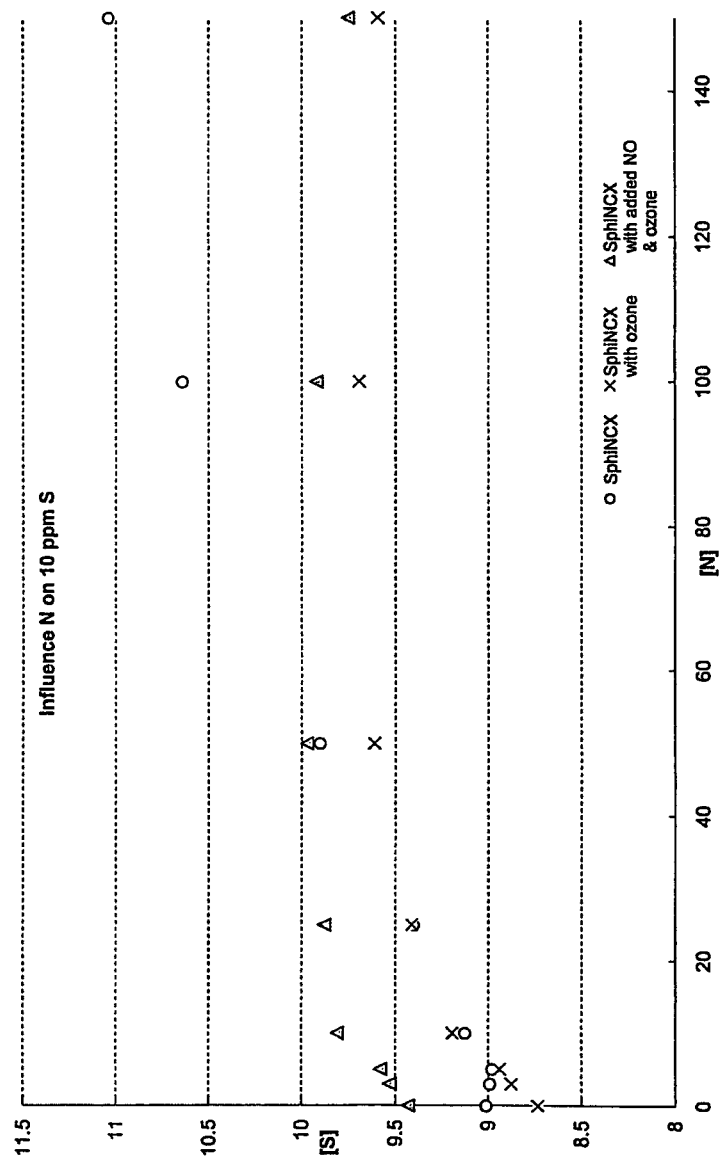
FIG. 4 shows a graph, illustrating the effects of adding a nitrogen compound into the combustion analyzer.

The results of the tests are shown in table 1 and on the graph of FIG. 4. The results for method A generally show a rise in the detected concentration of total sulphur in the eight standard samples, with increasing nitrogen in the samples. With no added nitrogen-containing liquid in the sample (sample 1), the yield of $SO_2$ was around 90%. The apparent yield of $SO_2$ for sample 8 was around 110%, clearly confirming that the UV fluorescence detector was measuring a signal from an interfering substance (NO), in addition to the $SO_2$.

TABLE 1

Influence of added nitrogen with different methods of determining sulphur on 10 ppm sulphur.

| | | | | | ppm | | | | |
|---|---|---|---|---|---|---|---|---|---|
| Added N | | 0 | 3 | 5 | 10 | 25 | 50 | 100 | 150 |
| Detected | A | 9.01 | 8.99 | 8.98 | 9.12 | 9.40 | 9.90 | 10.64 | 11.04 |
| S/ppm by | B | 8.74 | 8.88 | 8.94 | 9.19 | 9.41 | 9.61 | 9.69 | 9.59 |
| method: | C | 9.43 | 9.53 | 9.58 | 9.81 | 9.88 | 9.97 | 9.92 | 9.75 |

The results for method B do not show an ever-increasing detected concentration of total sulphur, with increasing nitrogen concentration in the samples. Provided sufficient ozone is mixed with the combustion products, substantially all NO can be removed from them. This means that the signal generated by the detector is substantially wholly from the fluorescence of $SO_2$ and indicates that the actual yield of $SO_2$ was around 87%. Accordingly, a calibration curve based on standard samples analyzed using method B may be obtained and used to provide total sulphur measurements of unknown samples, without interference from NO in the detector.

However, the yield of $SO_2$ is not consistent across samples 1 to 8, but varies from around 87% to around 96%, as the nitrogen concentration in the samples varies. The yield does appear to level off at around 95-96% from nitrogen concentrations in the sample of about 40-50 ppm and, before that, there is a reasonable yield, of over 90%, for nitrogen concentrations above about 10 ppm.

Nevertheless, the yield of $SO_2$ is affected by variations in the concentration of nitrogen in the samples. Since, for actual samples, the concentration of nitrogen is unknown and may vary between samples, a calibration curve obtained under method B would be an improvement on one obtained under method A, but still could not assure consistent applicability.

The results for method C are similar to those for method B, in that the detected concentration of total sulphur does not continue increasing with increasing added nitrogen concentration in the sample, but also levels out. However, the yield is shifted upwards for all samples and the levelling off of the yield occurs at lower sample concentrations of nitrogen. Also, the variation in detected sulphur concentrations across samples 1 to 8 is much reduced, giving a higher, more consistent yield of $SO_2$. The increase in yield from method B to method C varies from around 2% to around 7%, perhaps averaging around a 4% increase. This confirms that the additional NO in the combustion chamber is acting to encourage the formation of $SO_2$. The levelling off of the detected sulphur concentration takes place, at around 98-99%, from added nitrogen concentrations in the sample from around 20-40 ppm. The yield is considered to be good for all of the samples tested using the supplied $NO_x$ gas, whether or not a nitrogen-containing liquid was also added to the sample. The yield range, from around 94% to around 99%, is more consistent than that, of around 87% to around 96%, for method B.

The fact that there is still some variation in the detected total sulphur concentration for the method C results may be due to a number of factors. General variations in the measurement conditions may have had an effect, as may variations in the conditions under which the eight samples were prepared. Also, this may be down to how readily the nitrogen monoxide was mixed with the sample during combustion. It may be that the nitrogen-containing liquid added to the sample itself enables the NO, once formed, to have its yield-improving effect on $SO_2$ formation from the early stages of combustion, since it is already mixed with the sample. However, the $NO_x$ gas, which is pumped in and forms NO in the combustion chamber, first needs to mix with the sample while combustion is taking place. This may explain why the yield of $SO_2$ is lower for lower concentrations of nitrogen-containing liquid in the sample, even though an additional supply of NO is provided to the combustion chamber as $NO_x$ gas, so that there is a relatively high overall concentration of NO in the chamber.

Figure 5:
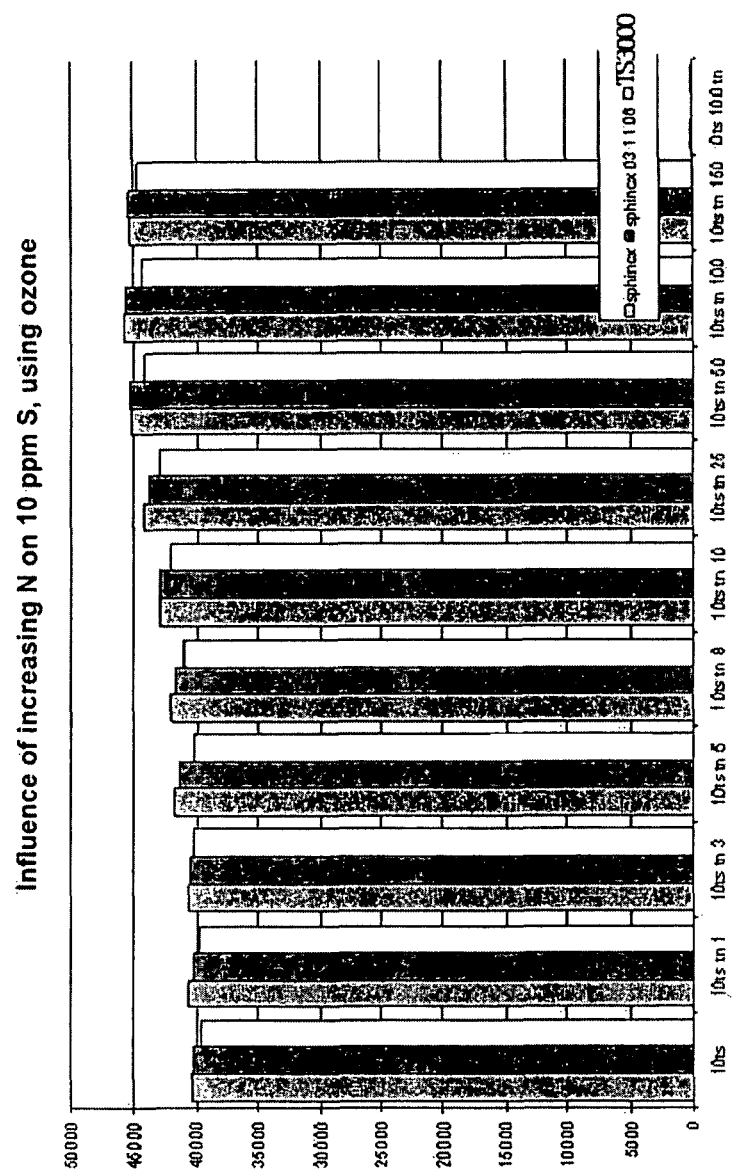
FIG. 5 shows a chart, illustrating the effects of adding a nitrogen compound into the combustion analyzer.

The second experiment is discussed in relation to FIG. 5. A number of known, standard samples were prepared. All of the samples were prepared with a 10 ppm sulphur concentration, except for the last which was prepared with a sulphur concentration of 0 ppm. The concentration of nitrogen-containing liquid in the sample was varied across the samples, from 0 to 150 ppm, the last sample however having a nitrogen concentration of 100 ppm. The sulphur-containing liquid used was thiophene in xylene and the nitrogen-containing liquid used was pyridine in xylene.

Two combustion analyzers configured to detect $SO_2$ by UV fluorescence detection, the SphiNCX and the TS3000 combustion analyzers, both manufactured by Thermo Fisher Scientific Inc., were modified to incorporate an ozone feed unit into the combustion products line between the combustion chamber and the detector, by means of a two-into-one connector. This allowed combustion products and ozone to mix and pass onwards to the detector. The oxygen flow to the ozonator was set by a flow controller to be 50 ml/min.

A respective amount of each sample was analyzed twice by the SphiNCX analyzer and once by the TS3000 analyzer. The results of each test are shown in table 2 and in the bar chart of FIG. 5 (in which, for the avoidance of doubt, for each sample, the results are ordered from left to right, from the SphiNCX analyzer 1, SphiNCX analyzer 2, and TS3000 analyzer, respectively). The results show a reasonably good correspondence between the detected levels from the analyzers, demonstrating that the invention may be applied to different sulphur-detecting combustion analyzers. The results also demonstrate, again, that the yield of $SO_2$ is improved by adding an amount of a nitrogen-containing liquid to the sample. It is evident that the yield of $SO_2$ appears generally to increase with any added nitrogen-containing yield improver.

From 10 to 50 ppm of added nitrogen-containing yield improver, the yield increases significantly. From around 50 ppm upwards the increase in $SO_2$ yield, if any, is less marked. The results indicate a general levelling off in the $SO_2$ yield above around 50 ppm added nitrogen in the sample.

TABLE 2

Influence of increasing nitrogen on 10 ppm sulphur, with different analyzers.

| Sample concentration TS/ppmTN/ppm | SphiNCX analyzer 1 area | SphiNCX analyzer 2 area | TS3000 analyzer area |
|---|---|---|---|
| TS 10 TN 0 | 40413 | 40294 | 39694 |
| TS 10 TN 1 | 40665 | 40262 | 39814 |
| TS 10 TN 3 | 40671 | 40529 | 40276 |
| TS 10 TN 5 | 41697 | 41288 | 40251 |
| TS 10 TN 8 | 41955 | 41652 | 40983 |
| TS 10 TN 10 | 42932 | 42968 | 42043 |
| TS 10 TN 25 | 44302 | 43808 | 42932 |
| TS 10 TN 50 | 45132 | 45275 | 44183 |
| TS 10 TN 100 | 45779 | 45671 | 44474 |
| TS 10 TN 150 | 45235 | 45395 | 44699 |
| TS 0 TN 100 | 76 | 0 | 96 |

The last sample—TS 0, TN 100—was tested to verify the effectiveness of the ozone. The results show that the ozone is able to remove substantially all NO formed or present in the combustion products, so that the detected signals for this sample are at the levels which are expected to be obtained for blank samples. For reference, the detected signal for sample 11 is about 0.2% of that for sample 9 (both of which had TN 100 ppm).

Figure 6:
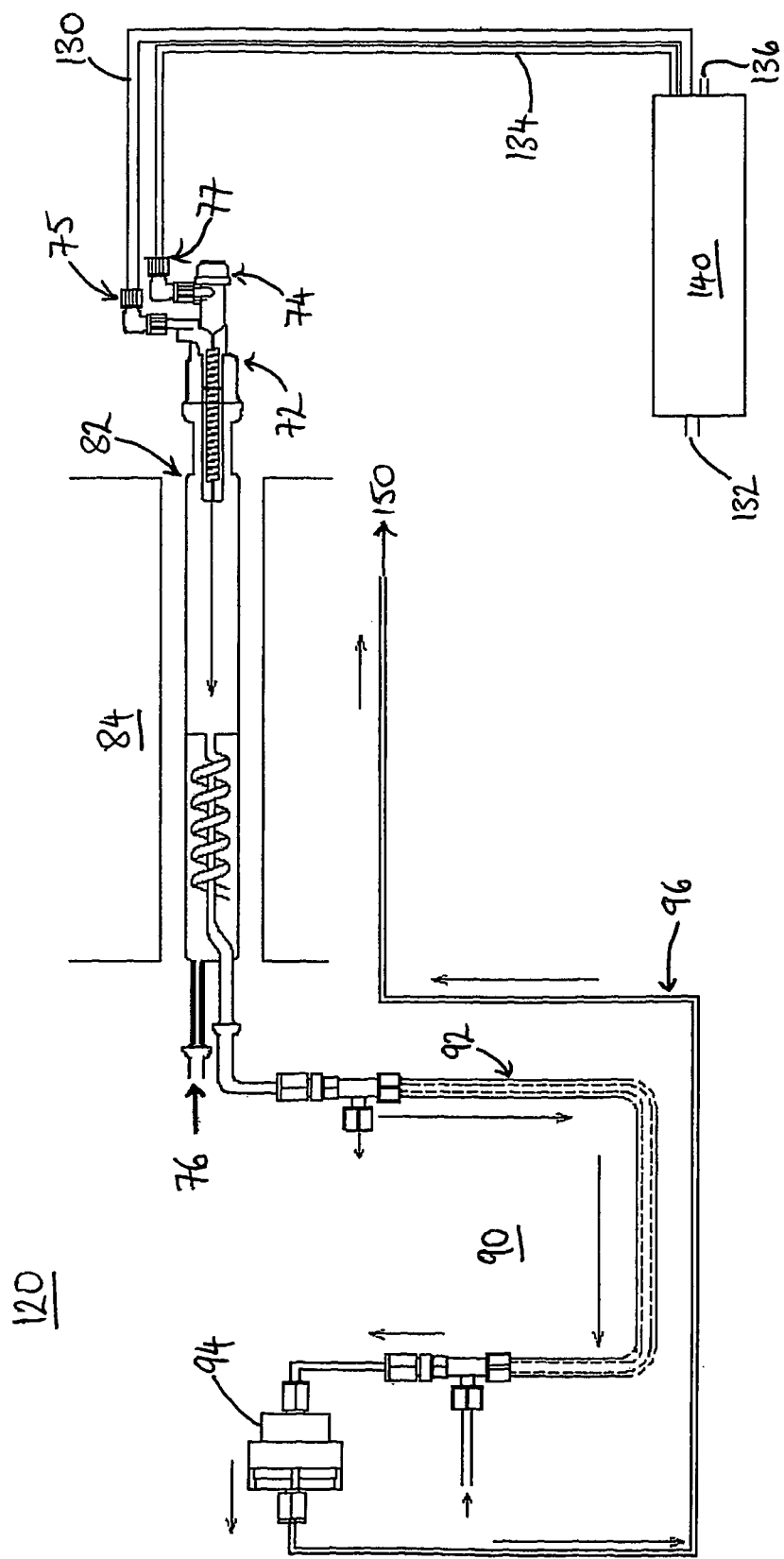
FIG. 6 shows a schematic layout of a combustion analyzer according to one embodiment of the invention.

FIG. 6 shows a schematic layout of a combustion analyzer 120, in accordance with one embodiment of the invention. The layout is generally the same as that for the analyzer shown in FIG. 2, with some alterations. Accordingly the same reference numerals have been used to describe the same, or functionally similar, apparatus parts.

The combustion analyzer 120 has an oxygen supply line 130 connected to the oxygen supply inlet 75. The oxygen supply line has an end 132 for connection to an oxygen feed unit (not shown). The combustion analyzer 120 has a carrier gas (typically argon) supply line 134 connected to the carrier gas supply inlet 77. The carrier gas supply line has an end 136 for connection to a carrier gas feed unit (not shown).

Installed on both the oxygen and the carrier gas supply lines 130, 134 is a yield improver feed unit 140. The yield improver feed unit 140 is configured to provide a supply of yield improver into one, both or none of the oxygen and carrier gas supply lines 130, 134. The yield improver feed unit 140 is connected to both supply lines 130, 134, by a switchable connector (not shown), which may be switched between various settings, depending on the application:

| Setting | Oxygen supply line | Carrier gas supply line |
|---|---|---|
| A | Oxygen | Carrier gas |
| B | Oxygen & yield improver | Carrier gas |
| C | Oxygen | Carrier gas & yield improver |
| D | Oxygen & yield improver | Carrier gas & yield improver |

In other embodiments, there may be more than one connector, which may or may not be switchable, between the yield improver feed unit 140 and the oxygen supply line 130 and the carrier gas supply line 134. In still others, a connector may be fitted only to one of the supply lines 130, 134. Whichever way, in this embodiment, the yield improver feed unit 140 is installed on, and therefore modifies, supply line tubing which is already on the outside of a combustion analyzer. In this way, the yield improver feed unit 140 may be relatively straightforwardly retrofitted to existing combustion analyzers which are used to detect sulphur concentrations.

The yield improver feed unit 140, in this embodiment, is configured to supply nitrogen oxide ($NO_x$) gas into one or both of the supply lines 130, 134. For a setting in which the yield improver feed unit 140 is connected or switched into only the oxygen supply line 130, a flow of oxygen passes into end 132 and, from the supply line 130, into the supply inlet 75 and on into the combustion chamber 82. A typical flow rate for the oxygen is between 200 and 400 ml/min. The $NO_x$ gas is pumped into the oxygen supply line 130 through the connector, where it mixes with the oxygen, for supply to the combustion chamber. A preferred flow rate for NO gas is between 15 and 50 ml/min. Such a flow rate is generally suitable to provide an abundance of NO in the combustion chamber before and/or during the combustion process, so that the yield of $SO_2$ in the combustion products is improved.

It is often generally known what the total sulphur concentration in a sample is, before measurement. For example, the sample may be taken from a high-grade chemical, or a food or beverage, or a petrochemical, each of which has a pre-defined, allowable total sulphur concentration. Even if the expected total sulphur concentration is in a working range between 0 and 100 ppm, the initial flow rate of NO gas can be set to correspond to a concentration of around 4-5 times the expected sulphur concentration and then reduced (or increased, if appropriate) for subsequent analyzes, once a first measurement of the total sulphur concentration has been made.

For example, once a combustion analyzer has been calibrated, any signal detected by a $SO_2$ UV fluorescence detector will look like fluorescence from $SO_2$, even if no sulphur-containing sample is being analyzed. NO gives a signal on total sulphur detectors, but at a signal level of about $1/100^{th}$ of that from sulphur dioxide (i.e., 100 ppm NO is 'seen' as about 1 ppm $SO_2$). Accordingly, if the working range of the analyzer is configured to detect total sulphur levels between 0 and 100 ppm, an initial flow rate for the $NO_x$ gas into the analyzer can be set so that the $SO_2$ detector measures a signal which looks like 4 ppm or more $SO_2$ (i.e., about 400 ppm of NO, which is around 4-5 times the expected total sulphur concentration). However, of course, the detected signal is not from $SO_2$, but from the deliberate NO interference passing into the detector. In practice, a pre-determined signal on the $SO_2$ detector will be known to represent a sufficient flow rate of NO into the analyzer for any particular analysis regime. For example, an arbitrarily selected signal level of 300 mV on the $SO_2$ UV fluorescence detector of the modified TS3000 combustion analyzer discussed above has been found to indicate that there is a sufficient flow of NO gas into the analyzer, to improve the $SO_2$ yield.

The combustion products formed in the combustion chamber 82—including an improved yield of $SO_2$—are carried through the conditioning stage 90 and along the combustion products line 96, by a general, background flow of carrier gas or oxygen through the analyzer 120. From the combustion products line 96, the combustion products are passed into one or more detectors 150 (not shown), one of which is configured to detect an amount of $SO_2$ therein.

The detector 150 for detecting $SO_2$ can be any suitable detector and is not limited to a UV fluorescence detector. For example, the detector 150 may be a coulometric detector using iodometric titration. In this case, the combustion gases containing $SO_2$ are passed through the electrolyte of a titration cell, containing tri-iodide ($I_3^-$). The sulphur dioxide reacts with the tri-iodide to form a sulphate and iodide. This reaction changes the potential from its pre-set value of the cell and this is detected. At the anode, iodide is reduced to iodine, to compensate for the tri-iodide deficiency, by an applied current. The current is integrated over time, providing a measurement of the amount titrated sulphur dioxide, from which the amount of sulphur in the sample may be calculated. The reaction equations for this process are:

$$6H_2O+SO_2+I_3^- \rightarrow SO_4^{2-}+3I^-+4H_3O^+$$

$$2I^- \rightarrow I_2+2e^- \} \text{ at the anode}$$

$$I_2+I^- \rightarrow I_3^- \} \text{ at the anode}$$

$$2H_3O+2e^- \rightarrow H_2+2H_2O \} \text{ at the cathode}$$

Since the invention improves the detectable sulphur yield by increasing the yield of $SO_2$ in the combustion gases, the invention may be applied to any combustion analyzer employing a sulphur dioxide detection mechanism and provide corresponding advantages thereto.

In some of the tests discussed above, an ozone feed unit was employed to remove any NO present in the combustion gases, before they were detected. Such a feed unit is not required when the detector 150, used to detect the $SO_2$ concentration, is not affected by NO interference. For example, it would not be required when a coulometric detector is used. It may also not be required if the yield improver used is not one which forms NO in the combustion products. Furthermore, it may be desirable not to mix ozone with the combustion products, even when a UV fluorescence detector is used. This may be so that evaluation or reference measurements may be made, or so that a total nitrogen chemiluminescence detector may be employed following the $SO_2$ detector.

Figure 7:
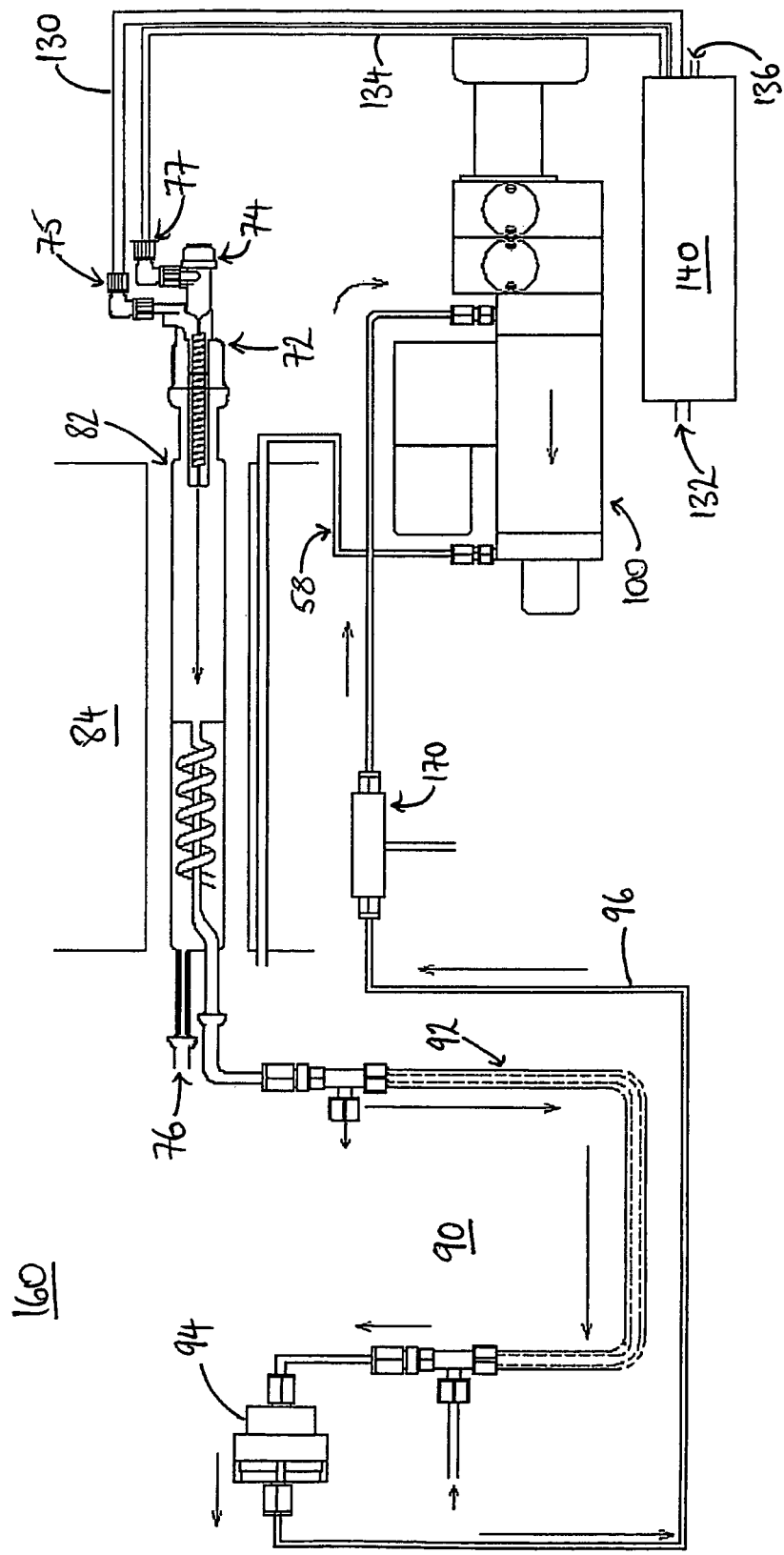
FIG. 7 shows a schematic layout of a combustion analyzer according to another embodiment of the invention.

Having said that, where a UV fluorescence detector 100 is used, it is preferable to add an ozone feed unit 170 onto the combustion products line 96. Such an embodiment is shown in FIG. 7. The combustion analyzer 160 has a yield improver feed unit 140 installed on the oxygen and/or carrier gas supply lines 130, 134, an ozone feed unit 170 installed on the combustion products line 96, which leads into a UV fluorescence detector 100. An ozonator (also known as an ozonizer) is preferably employed as the ozone feed unit 170.

The combustion analyzer 160 may be operated generally in the same manner as described with reference to FIG. 6, but modified to mix ozone into the combustion products, as described for methods B and C of the first experiment (FIG. 4), or for the second experiment (FIG. 5), above. Preferably, the ozone is supplied at a flow rate of 50 ml/min, but may be supplied at any suitable rate to have its NO interference removal effect.

The ozone mixed into the combustion products should preferably be supplied in a greater quantity than is needed to remove all NO gas, to help ensure substantially all NO gas is converted to $NO_2$. Since ozone is toxic, it should preferably not simply be pumped to waste. Accordingly, the combustion analyzer 160 has a waste discharge line 58, which passes through or near to the combustion chamber heater 84. In this way, ozone present in the waste products from the detector 100 may be thermally dissociated into oxygen before being discharged from the analyzer. Other techniques for ozone removal may alternatively be employed.

Figure 8:
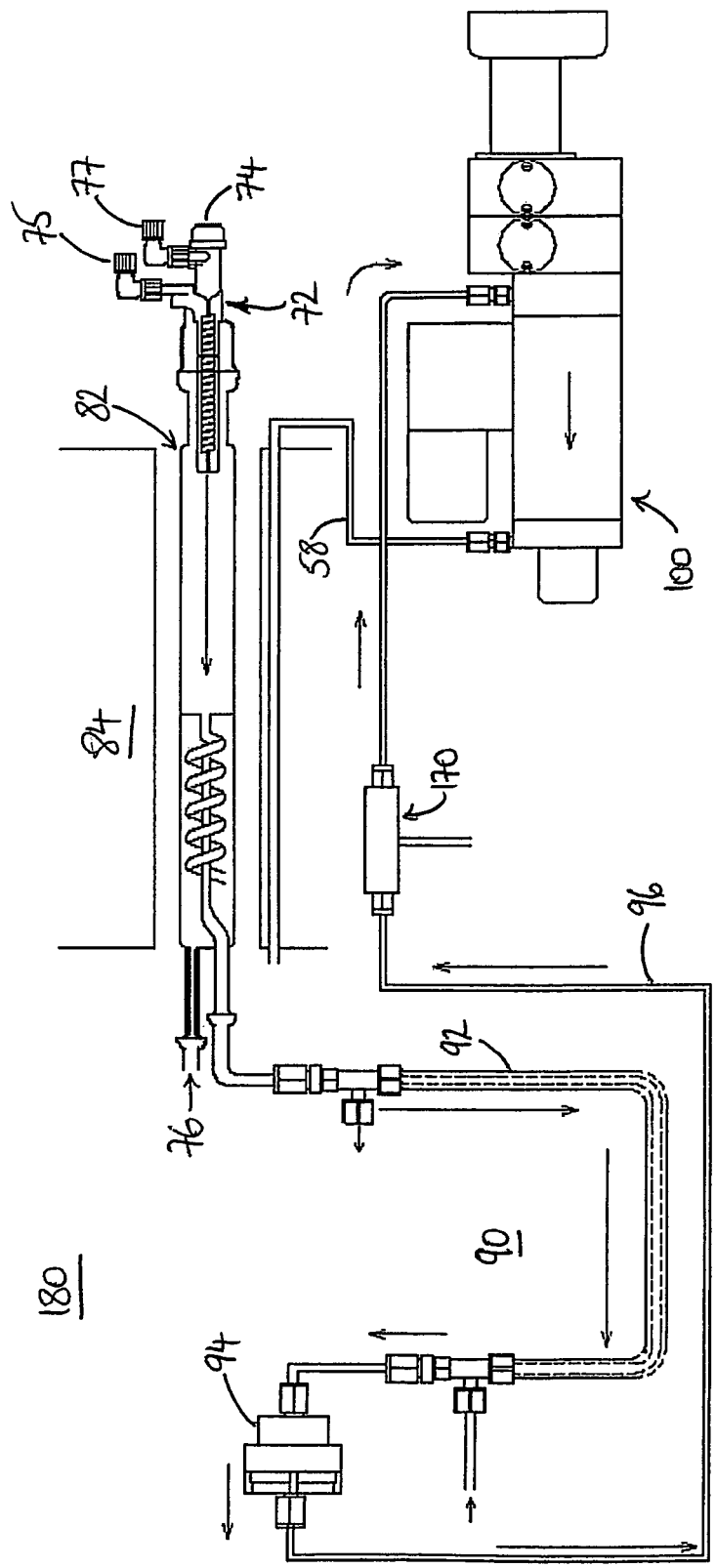
FIG. 8 shows a schematic layout of a combustion analyzer according to a further embodiment of the invention.

FIG. 8 shows a combustion analyzer 180, according to a further embodiment of the invention. The embodiment of FIG. 8 is similar to that of FIG. 7, except that a yield improver feed unit is not included. That is, the combustion analyzer 180 is configured in a similar manner to the analyzer shown in FIG. 2, but has been modified to incorporate an ozone feed unit 170. The combustion analyzer 180 may be operated generally in the same manner as described with reference to FIG. 2, but modified to mix ozone into the combustion products, as described for method B of the first experiment (FIG. 4), or for the second experiment (FIG. 5), above. Preferably, the ozone is supplied at a flow rate of 50 ml/min, but may be supplied at any suitable rate to remove any NO interference. This embodiment may be used when a nitrogen-containing yield improver is added to a sample either as a liquid or a (powdered) solid, or when no yield improver is added, and it is desired that any residual NO gas be removed from the combustion products before detection.

As described above, the yield improver may be provided by nitrogen monoxide gas or $NO_x$ gas, which may be supplied either directly into a combustion chamber, or into the gas supply line for oxygen or a carrier gas into the combustion chamber. The nitrogen monoxide or $NO_x$ may simply be supplied from a gas bottle/cylinder. Alternatively, the nitrogen monoxide may be obtained from a $NO_x$ generator, configured to generate and then supply $NO_x$ into the combustion chamber via any of the above routes. In operation, at the typical temperature of the combustion chamber (around 1000° C.), substantially all oxides of nitrogen are formed into nitrogen monoxide, so the $NO_x$ generated by the $NO_x$ generator serves as a source of nitrogen monoxide yield improver.

A $NO_x$ generator may be provided by a purposefully configured ozonator. An ozonator (also known as an ozonizer) is an apparatus for the preparation of ozone by passing oxygen through an electrical discharge. It has been found that passing nitrogen and oxygen through such an electrical discharge in an ozonator can produce sufficient quantities of $NO_x$ to be used as a source of nitrogen monoxide for the combustion analyzer. Advantageously, ambient air (preferably filtered and dried) can be used as the source of the nitrogen and oxygen into the ozonator.

The $NO_x$ generator is described in detail in our co-pending application, entitled "Apparatus and method for generating nitrogen oxides", and filed on even date herewith, under attorney docket number AJF/DP/P90252 and claiming priority from GB0626031.9, the entirety of which is incorporated herein by reference.

It has been shown that NO, either pumped into the combustion chamber or formed from a nitrogen-containing liquid added to the sample, increases the yield of $SO_2$ in the combustion products. It has also been shown that, by mixing ozone with the combustion products prior to detection, it is possible to remove substantially all NO (whether from the sample or added $NO_x$ gas) from the combustion products. According to embodiments of the invention, then, it is possible to increase the $SO_2$ yield and to improve the accuracy of the $SO_2$ detection.

Since variations in the amount of nitrogen monoxide in the analyzer affect the yield of $SO_2$, it is preferable to supply NO or a source thereof to the analyzer in sufficient quantities that any variations in nitrogen-containing substance actually present in the (unknown) sample have a negligible effect on the yield of $SO_2$, since the influence of the supplied NO or its source on the yield will be much more significant.

As stated above, total sulphur combustion analyzers cannot make absolute measurements because the sulphur in a sample is not completely converted into $SO_2$. A calibration curve is therefore necessary and it is important that the known, standard samples used to obtain the calibration curve are analyzed under the same conditions as unknown samples, otherwise the results will not be accurate. By providing an excess concentration of NO in the analyzer, preferably around 4-5 times the expected concentration of sulphur in the sample, not only a substantially consistent yield, but also an increased yield, of $SO_2$ may be achieved. This principle applies to all total sulphur combustion analyzers.

The above description has focused on the use of nitrogen monoxide to improve the yield of sulphur dioxide in the combustion products. The yield improver may be supplied as nitrogen monoxide gas into the combustion analyzer. Alternatively, a nitrogen-containing substance may be supplied to the combustion analyzer, such that the substance forms nitrogen monoxide therein. Where the yield improver is a source of nitrogen monoxide, one or more of the following may be used: pyridine, benzonitrile, nitrogen dioxide, general nitrogen oxides ($NO_x$), ammonia, and 2-ethylhexyl nitrate. Other suitable nitrogen-containing substances may alternatively be used, provided that nitrogen monoxide may be produced therefrom. With the supply of nitrogen dioxide, or $NO_x$, at temperatures of over 1000° C., as generally provided in the combustion chamber 82, substantially all forms of nitrogen oxides are converted to nitrogen monoxide.

Suitable yield improver alternatives may be verified by carrying out experiments similar to those discussed above, with reference to FIGS. 4 and 5.

Depending on the yield improver employed, the yield improver may be supplied to the combustion analyzer in gaseous, vaporous, liquid, or solid (preferably powdered) form. A gaseous yield improver may be pumped directly into the combustion chamber, via a dedicated inlet. Such inlet may be similar to that used for the additional oxygen supply 76, although the dedicated inlet for the yield improver may be located at any suitable position at either end of the combustion chamber 82. Alternatively, and more straightforwardly, the gaseous yield improver may be supplied into one of the oxygen or carrier gas supply lines 130, 134, as described above. The above possibilities also apply to a vaporous yield improver.

For a liquid yield improver, the yield improver may simply be added to the sample, before or as the sample is supplied to the combustion analyzer, for introduction into the combustion chamber 82. Alternatively, the liquid sample may be injected directly into the combustion chamber 82, before or during combustion. Again, this may be by means of a dedicated injector inlet. Alternatively, the liquid yield improver may be supplied into, and entrained by, either the oxygen or carrier gas flows, along their respective lines 130, 134.

Of course, as already described with some of the embodiments above, more than one of the above techniques for supplying the yield improver to the combustion analyzer may be used together, if desired. For example, liquid yield (such as pyridine, benzonitrile and 2-ethylhexyl nitrate) improver may be added to the sample before detection and gaseous yield improver may be supplied to the combustion chamber before and/or during combustion.

As shown empirically in the above experiment, a sulphur dioxide yield improvement is achieved when the proportion of yield improver is greater than an expected proportion of sulphur in the combustion analyzer. FIG. 4 shows that a relative proportion of yield improver to expected sulphur of 2 to 1 or above provides a significant yield improvement. Between 4 and 5 to 1, the yield of sulphur dioxide does not increase so rapidly, but starts to level off. Nonetheless, for certain types of sample or entirely unknown samples, it may be preferable to supply yield improver to the combustion analyzer with a ratio of yield improver to expected sulphur proportions of up to 25-50 to 1, or even 100 to 1. For example, with a low-range detector, detecting around 0 to 100 ppm sulphur, an abundance of yield improver may be considered to be present in the combustion analyzer, when there is around 1000 ppm of the yield improver.

Preferably, the yield improver is supplied before or during combustion.

Where ozone is added to the combustion analyzer, the preferred flow rate is 50 ml/min. However, the ozone flow rate may be between approximately 0.5 and 1 ml/s, or any other suitable flow rate for removing interfering nitrogen monoxide from the combustion products.

The invention may be applied to all combustion analysis instruments, which detect total sulphur by measuring sulphur dioxide levels. This applies to dedicated total sulphur instruments, which are configured only to measure total sulphur. This also applies to multi-use instruments, which are configured to detect total sulphur as well as other components of a sample. For example, total sulphur and total nitrogen instruments are known and this invention may be applied to them.

A TS+TN instrument may be configured firstly to combust a first sample, secondly to measure the total sulphur in that first sample, and thirdly to measure the total nitrogen in that first sample. Alternatively, the instrument may be configured to combust a first sample and detect the total sulphur in that first sample, then to combust a second sample and to detect the total nitrogen in that second sample, where the first and second samples are of identical composition.

Where the same combustion sample is detected by both detectors, the total sulphur must be measured before the total nitrogen. This is because sulphur dioxide is adsorbed by the material, stainless steel, used in the detector tubing and chamber for a total nitrogen detector. Accordingly, if the total nitrogen were measured first, the subsequent total sulphur measurement would be compromised. As such, where total sulphur is measured, with added nitrogen monoxide to improve the yield and added ozone to remove the nitrogen monoxide, a total nitrogen measurement is not then possible, since substantially all of the nitrogen monoxide in the combustion products is removed by the ozone. The combustion analyzer is therefore preferably switchable, so that the addition of a yield improver and/or supply of ozone may be turned on and off, as desired. A first sample can be analyzed with the option on, so improving the detection of sulphur dioxide; and a second, identical sample can be analyzed with the option turned off, so that total nitrogen may be measured. For the second sample, the total sulphur could also be measured at the same time, but this measurement would suffer from the possible problems of inconsistent sulphur dioxide yield and nitrogen monoxide interference.

In view of the fact that total sulphur detection must take place before total nitrogen detection in a combined combustion analyzer, the introduction of an ozone feed unit to the combustion products line leading to the $SO_2$ detector and the addition of ozone to the combustion products before detection by the $SO_2$ detector are considered to be new and advantageous aspects of the invention.

The invention may be employed for various applications in, for example, the chemical, refinery, hydrocarbon, petrochemical, and food and beverage sectors. The invention may be used in the analysis of solid, high-viscosity, liquid or gaseous samples. In particular, the invention may be used in the analysis of refinery products, such as gasoline and diesels.

The invention claimed is:
1. A combustion analyzer for combustion analysing a sample comprising a proportion of sulphur, the analyzer comprising:

a combustion chamber comprising an inlet end and another end, the inlet end for receiving a sample for combustion therein to form combustion products, the combustion products comprising a yield of sulphur dioxide; and a detector receiving the combustion products from the other end of the combustion chamber for detecting an amount of sulphur dioxide in the combustion products, characterised by further comprising a yield improver supply apparatus for supplying a sulphur yield improver to the inlet end of the combustion chamber, wherein the yield improver includes one or more of the group consisting of pyridine, benzonitrile, nitrogen dioxide, general nitrogen oxides (NOx) and 2-ethylhexyl nitrate.

2. The analyzer of claim 1, further comprising a yield improver supply line to the combustion chamber inlet end, wherein the yield improver supply apparatus has a connection to the supply line and is arranged to supply a sulphur yield improver to the combustion chamber therethrough.

3. The apparatus of claim 1, further comprising an oxygen supply line to the combustion chamber inlet end, wherein the yield improver supply apparatus has a connection to the supply line and is arranged to supply a sulphur yield improver to the combustion chamber through that supply line.

4. The apparatus of claim 1, further comprising a carrier gas supply line to the combustion chamber inlet end, wherein the yield improver supply apparatus has a connection to the supply line and is arranged to supply a sulphur yield improver to the combustion chamber through that supply line.

5. The apparatus of claim 1, wherein the yield improver supply apparatus is switchable between a first on state in which a sulphur yield improver may be supplied to the combustion analyzer and a first off state in which a sulphur yield improver may not be supplied to the combustion analyzer.

6. The apparatus of claim 1, further comprising an ozone supply apparatus arranged to supply ozone to a region of the combustion analyzer, the region being after the combustion chamber, in the detector or therebetween.

7. The apparatus of claim 6, wherein the ozone supply apparatus is switchable between a second on state in which ozone may be supplied and a second off state in which ozone may not be supplied.

8. The analyzer of claim 2, wherein the yield improver supply line comprises a liquid supply line for supplying a liquid yield improver to the combustion chamber inlet end.

9. The analyzer of claim 8, further comprising a dedicated injector inlet for supplying the liquid yield improver to the combustion chamber inlet end, the injector inlet having a connection to the liquid supply line.

10. A combustion analyzer for combustion analysing a sample comprising a proportion of sulphur, the analyzer comprising:

a combustion chamber comprising an inlet end and another end, the inlet end for receiving a sample for combustion therein to form combustion products, the combustion products comprising a yield of sulphur dioxide;

a detector receiving the combustion products from the other end of the combustion chamber for detecting an amount of sulphur dioxide in the combustion products;

a first yield improver supply apparatus for supplying a gaseous yield improver to the inlet end of the combustion chamber, wherein the gaseous yield improver is nitrogen monoxide or a gaseous source of nitrogen monoxide; and a second yield improver supply apparatus for supplying a liquid yield improver to the inlet end of the combustion chamber, wherein the liquid yield improver includes one or more of the group consisting of pyridine, benzonitrile and 2-ethylhexyl nitrate.

\* \* \* \* \*